United States Patent [19]
Bernhardt et al.

[11] Patent Number: 5,830,638
[45] Date of Patent: Nov. 3, 1998

[54] CELL LINE AND PROCESSES FOR THE REPLICATING RABIES VIRUSES AND DETECTING THEM QUANTITATIVELY

[75] Inventors: Dieter Bernhardt, Cölbe; Albrecht Gröner, Seeheim, both of Germany

[73] Assignee: Behringwerke Aktiengesellschaft, Marburg, Germany

[21] Appl. No.: 913,317

[22] PCT Filed: Jan. 30, 1996

[86] PCT No.: PCT/EP96/00424

§ 371 Date: Sep. 12, 1997

§ 102(e) Date: Sep. 12, 1997

[87] PCT Pub. No.: WO96/30499

PCT Pub. Date: Oct. 3, 1996

[30] Foreign Application Priority Data

Mar. 31, 1995 [DE] Germany ............ 195 12 057.4

[51] Int. Cl.⁶ .......... A61K 39/208; C12N 7/00; C12N 7/08
[52] U.S. Cl. ............ 435/5; 435/237; 435/235.1; 435/325; 435/236; 424/224.1
[58] Field of Search ............... 435/325, 5, 236, 435/237, 238

[56] References Cited

U.S. PATENT DOCUMENTS 4,664,912   5/1987   Wiktor et al. .

OTHER PUBLICATIONS

Cleide A. Consales et al., "Cytopathic effect induced by rabies virus in McCoy cells", Journal of Virological Methods, 27, pp. 277–286 (1990).

J. Egert et al., "Properties of Rabies Strain (,, Pasteur Potsdam) Adapted to Primary Dog Kidney Cells", Acta virol. 33:553–558 (1989).

Abigail L. Smith et al., "Isolation and Assay of Rabies Serogroup Viruses in CER Cells", Intervirology 8:92–99 (1977).

*Primary Examiner*—Michael P. Woodward
*Assistant Examiner*—Rebecca Fuldner
*Attorney, Agent, or Firm*—Finnegan, Henderson, Farabow, Garrett & Dunner, L.L.P.

[57] ABSTRACT

A permanent cell line PH2, and a process for replication of rabies viruses which have a cytopathic effect (CPE) is claimed. The process comprises: infecting the PH2 cell line with the virus to be replicated; incubating the cells; and isolating and purifying virus particles after they have reached a sufficiently high titer.

6 Claims, No Drawings

CELL LINE AND PROCESSES FOR THE REPLICATING RABIES VIRUSES AND DETECTING THEM QUANTITATIVELY

The invention relates to a permanent cell line and a process for replicating infectious rabies virus and to its quantitative detection by means of the cytopathic effect (CPE) using this cell line, and to a process for detecting inhibitors of rabies virus replication.

Living cells are required in order to produce proteins and viral antigens. In the state of the art, diploid cell strains or permanent cell lines are used for this purpose provided they are suitable for producing the desired proteins or viral antigens. As compared with diploid cell strains, permanent cell lines enjoy the advantage that they exhibit unlimited growth, i.e. they are immortalized. Over broad passage ranges, such permanent cell lines exhibit constant properties as regards cell and antigen replication since, in their case, no cell differentiation takes place as it does in diploid cell strains. Apart from the limited lifespan (passage number) of diploid cell strains, a further, serious disadvantage of these strains is that the organs, tissues, and also chick embryos, which are required as starting material for diploid cell strains are not available in adequate quantity and at all times. Furthermore, the starting material can be latently and/or inapparently contaminated (viruses, mycoplasmas and bacteria), as a result of which optimally reproducible antigen production is not guaranteed.

While it is known that rabies virus can be replicated in cell cultures derived from a multiplicity of species, there are only a few reports in the literature of a cytopathic effect being obtained (Egert et al., Acta Virol. 33 (1989), 353–358, Consales et al., J. Virol. Meth. 27 (1990), 227–286, Campbell and Charlton, in: Development in veterinary virology: Rabies Kluwer Academic Publishers, Boston, Dordrecht, London, 1988). The cytopathic effect (CPE) is a virally-determined, specific cell destruction (lysis) which can readily be detected under the light microscope.

In general, however, replication of rabies virus in tissue cultures either proceeds without any CPE (Campbell and Charlton (1988)) or else virally-determined cytopathic changes are only irregular (Kaplan and Koprowski, Laboratory techniques in rabies, III. Edit. Wld. Hlth. Org. Monograph Series 23, Geneva (1973)) or only occur transiently (Smith et al., Intervirol. 8 (1977), 92–99), so that rabies viruses cannot be detected reliably by evaluating the CPE when these cell lines are used.

The present invention was therefore based on the technical problem of providing a permanent cell line and processes which do not exhibit these disadvantages, i.e. which generally enable infectious rabies viruses to be replicated with an improved yield and with the appearance of the cytopathic effect (CPE), which can be used to detect them quantitatively in a sensitive manner.

This technical problem is solved by the provision of the embodiments which are characterized in the claims.

It has been found, surprisingly, that rabies viruses having a cytopathic effect (CPE) replicate in high yields in the novel permanent cell line PH-2. Other virus species from different virus families, such as picornaviruses, herpesviruses, paramyxoviruses, reoviruses and togaviruses, can likewise be replicated in this cell line. This cell line is suitable both for the production of virus antigens and for virus and antibody detection. It is particularly surprising that rabies virus, which belongs to the rhabdoviruses, always produces a cytopathic effect (CPE) when it is replicated in this cell line, as a result of which this cell line is particularly suitable for the simple detection and for the quantitative determination of rabies virus and (neutralizing) rabies virus antibodies.

Consequently, the invention relates to the permanent cell line PH-2 and to cell lines which are derived therefrom. The cell line PH-2 has been deposited in the DSM Deutsche Sammlung für Mikroorganismen (German Collection of Microorganisms) in Braunschweig under number DSM ACC 2165.

In a preferred embodiment, the present invention relates to a process for replicating rabies viruses which have a cytopathic effect, which comprises infecting the novel cell line with the virus to be replicated and incubating it under suitable conditions and isolating and purifying virus particles after they have reached a sufficiently high titer.

Methods which are known in the state of the art, for example ultracentrifugation, ultrafiltration, chromatography and the like, can be used to isolate and purify virus antigens from the virus particles which have been obtained in this way and then chemically or physically disintegrated. These antigens which have been obtained in this way can be used, inter alia, to prepare a vaccine or for diagnostic purposes. In a further preferred embodiment, the present invention consequently relates to a process for obtaining rabies virus particles, which comprises isolating and purifying viral antigens from the virus particles after they have been obtained.

The fact that rabies viruses can not only be replicated more efficiently when using the novel cell line than when using cell lines which are known from the state of the art, but that a cytopathic effect also occurs at the same time, renders it possible to detect rabies viruses in samples in a sensitive and simple manner and to determine them quantitatively.

A further preferred embodiment, therefore, relates to a process for detecting rabies viruses on the basis of the cytopathic effect, which comprises bringing the novel cell line into contact with a sample which is suspected of containing the rabies virus to be detected, incubating the cells and detecting the replicating virus by means of microscopic determination of the CPE. In order to carry out this process, the virus sample is, for example, added to a cell culture which is sown in microtiter plates or other cell culture vessels which are known to the person skilled in the art and either left until the end of the experiment or removed after a given adsorption time together with the cell culture medium and replaced by fresh cell culture medium. The cell cultures are examined regularly, for example up to the 5th to 7th day, after the inoculation, for CPE using a light microscope.

In a particularly preferred embodiment, the sensitivity of detection in the novel detection process is approximately one $\log_{10}$ step higher as compared with the state of the art (fluorescence-antibody technique (FITC)).

In addition to this, inhibitors of viral replication can also be determined using the novel cell line. These inhibitors can be active at all stages of viral replication—adsorption/penetration, virus nucleic acid uncoating, transcription and translation as well as post-translational protein modification, virus assembly and budding. In this context, the inhibitors can be, for example, neutralizing antibodies, chemical or biological ligands against viral and cell receptors, chemotherapeutic agents or interferon or other cytokines. Inhibition of viral replication can be readily detected by the absence of a CPE in the claimed cell line. The person skilled in the art knows how to conduct an experiment for detecting an inhibition.

Consequently, the present invention also relates to a process for detecting inhibitors of rabies virus replication, which comprises detecting inhibition of the replication of the virus in the novel cell line, in the presence of the inhibitor, by the absence of the CPE.

The following examples illustrate the invention.

EXAMPLE 1

Obtaining the PH-2 cell line

In order to develop the permanent cell line PH-2, primary equine skin cells were mixed with a few permanent monkey kidney cells (Vero M) which had been replicated at the same time in the laboratory. When this was done, cells which were morphologically distinguishable from the Vero cells surprisingly overgrew the equine skin fibroblasts. These cells were isolated and designated PH-2 cells.

The karyotyping of the PH-2 cell is compared with that of the Vero M cell in Table 1. The PH-2 cell differs from the Vero M cell in its chromosome complement and in its chromosome distribution pattern.

TABLE 1

| | | Chromosome distribution | | |
|---|---|---|---|---|
| | Number of chromosomes | meta-centric | submetacentric + subtelecentric | acrocentric + telocentric |
| Vero cell line | 55 | 19 | 21 | 15 |
| PH-2 cell line | 56 | 20 | 27 | 9 |

Rabies virus replicates in the PH-2 cell line with the production of a CPE, which is not the case in the starting cell line (Vero).

EXAMPLE 2

Comparative titration of rabies virus, strain Flury LEP (ATCC VR-138), in chick fibroblast cultures (standard method) and PH-2 cell cultures.

Virus which had been replicated in chick fibroblast cultures was obtained as a standard product of Behringwerke AG.

Chick fibroblast cells were sown in microtiter plates, in accordance with the protocol, 24 hrs before applying the virus titer. PH-2 cells were deposited in the microtiter plates immediately before commencing the titration. In the case of the chick fibroblasts, the medium for sowing the cells was Medium 3 containing 1% fetal calf serum (FCS) and NSP, while in the case of the PH-2 cells it was EME Medium and 2% FCS and NSP. The rabies virus was diluted in Medium 3 in $\log_{10}$ steps. For each dilution step, 8 wells of the corresponding culture type were inoculated with 200 $\mu$l of the dilution/well. The cultures were then incubated at 37° C. in a $CO_2$ incubator.

In the case of the chick fibroblast cultures, the titers were read at from 3 to 5 days after starting the test, once the cells had been stained with FITC-labeled antibodies (fluorescence method); in the case of the PH-2 cultures, they were read microscopically, on the 5th to 7th day after beginning the test, on the basis of the CPE which had been caused by the rabies virus. The titers were calculated by the Kärber method.

The results of the comparative titrations are recorded in Table 2 below.

TABLE 2

| | Titer in $\log_{10}$/ml | |
|---|---|---|
| Experiment No. | in chick fibroblasts | in PH-2 cells |
| 1 | 8.0 | 9.0 |
| 2 | 7.7 | 8.8 |
| 3 | 7.5 | 8.6 |
| 4 | 7.9 | 8.2 |
| 5 | 7.1 | 8.0 |
| 6 | 6.7 | 7.5 |
| 7 | 6.0 | 7.2 |
| 8 | 4.8 | 6.0 |
| 9 | 4.1 | 5.2 |
| 10 | 3.0 | 4.8 |
| 11 | 2.3 | 4.0 |
| Test evaluation | Fluorescence-antibody technique | CPE |

As is evident from the comparative investigations, the titers which are determined in PH-2 cells by means of microscopic detection are on average one $\log_{10}$ step higher than the titers found in chick fibroblasts. This demonstrates that, in addition to considerably simplifying the procedure for detecting rabies virus, this method is also appreciably more sensitive than the detection methods which are available within the state of the art.

EXAMPLE 3

Rabies virus replication in PH-2 cells (replication curve)

PH-2 cells which had been densely grown in Roux dishes were infected, after changing the medium to EME Medium without serum, with rabies virus at a multiplicity of infection of 0.01 and incubated at 37° C. Samples were removed from the infected Roux dish after the time intervals indicated in Table 3 and the content of infectious virus particles was determined. The values which were found are listed below in Table 3.

TABLE 3

| | 0 | 1 | 3 | 4 | 5 | 6 | 7 |
|---|---|---|---|---|---|---|---|
| Titer/ml in $\log_{10}$ | 4.5 | 4.5 | 7.4 | 7.5 | 8.0 | 8.3 | 7.4 |

As is evident from the values in Table 3, rabies virus can be replicated to high titers in the PH-2 cell line. This cell line is thus very well suited for producing rabies virus antigen.

EXAMPLE 4

Testing the reproducibility of rabies virus titer in different PH-2 passages

The same rabies virus preparation, the Flury LEP strain, was used to determine the titer in the 36th, 85th and 100th passage of the PH-2 cells.

Table 4 below contains the results of the experimental series.

TABLE 4

| PH-2 | Rabies virus titer in $\log_{10}$/ml | | |
|---|---|---|---|
| passage | Experiment 1 | Experiment 2 | Experiment 3 |
| 36 | 6.9 | 6.9 | 7.1 |
| 85 | 6.5 | 6.9 | 7.1 |

TABLE 4-continued

| PH-2 | Rabies virus titer in $log_{10}$/ml | | |
|---|---|---|---|
| passage | Experiment 1 | Experiment 2 | Experiment 3 |
| 100 | n.i. | 6.9 | 6.9 |

As is evident from the results in this table, the sensitivity of the PH-2 cell line toward rabies virus remains unchanged in the passage ranges which were tested, i.e. between the 36th and 100th passage.

We claim:

1. A permanent cell line having the designation PH-2 (deposition no. DSM ACC2165), or a cell line derived therefrom.

2. A process for replicating rabies viruses which have a cytopathic effect (CPE), which comprises a) infecting the cell line as claimed in claim 1 with the virus to be replicated;

b) incubating the cells; and c) isolating and purifying virus particles after they have reached a sufficiently high titer.

3. The process as claimed in claim 2, wherein, furthermore, after step c), the viral antigens are isolated from the virus particles and purified.

4. A process for detecting rabies viruses which comprises:

a) contacting PH-2 cells (DSM ACC 2165) or a cell line derived therefrom with a sample which is suspected of containing the rabies virus to be detected;

b) incubating the cells; and c) determining the presence of said rabies virus, by means of microscopically ascertaining the CPE caused by the virus infection.

5. The process as claimed in claim 4, wherein the sensitivity of detection is approximately one $log_{10}$ step higher than the standard fluorescence-antibody technique (FITC).

6. A process for detecting inhibitors of rabies virus replication which comprises:

detecting inhibition of the replication of the virus in PH-2 cells (DSM ACC 2165) or a cell line derived therefrom by the absence of CPE following incubation of said cells in the presence of a suspected inhibitor and rabies virus.

* * * * *